US00PP37099P2

(12) United States Plant Patent
Scheiber

(10) Patent No.: US PP37,099 P2
(45) Date of Patent: Nov. 18, 2025

(54) ***HYDRANGEA* PLANT NAMED 'Age3213ens'**

(50) Latin Name: *Hydrangea arborescens*
Varietal Denomination: Age3213ens

(71) Applicant: The Conard Pyle Company, West Grove, PA (US)

(72) Inventor: Sloane Michele Scheiber, West Grove, PA (US)

(73) Assignee: The Conard Pyle Company, West Grove, PA (US)

( * ) Notice: Subject to any disclaimer, the term of this patent is extended or adjusted under 35 U.S.C. 154(b) by 0 days.

(21) Appl. No.: 19/004,873

(22) Filed: Dec. 30, 2024

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
See application file for complete search history.

(56) References Cited

U.S. PATENT DOCUMENTS

PP20,571 P2 12/2009 Wood
PP28,316 P3 8/2017 Ranney

OTHER PUBLICATIONS

Star Roses and Plants 2025 Catalog, Woody Ornamentals & Edibles (Oct. 7, 2024).

*Primary Examiner* — Shubo Zhou
*Assistant Examiner* — Zachariah Allan Kay
(74) *Attorney, Agent, or Firm* — Panitch Schwarze Belisario & Nadel LLP; Stephany G. Small; Travis W. Bliss

(57) ABSTRACT

A new and distinct cultivar of *Hydrangea* plant, referred to by its cultivar name, 'Age3213ens', is disclosed. The new variety forms bright white colored mophead-type flowers and green foliage is formed. The new variety displays a compact growth habit. The new variety is well suited for providing distinguished ornamentation in the landscape.

2 Drawing Sheets

Figure 1:
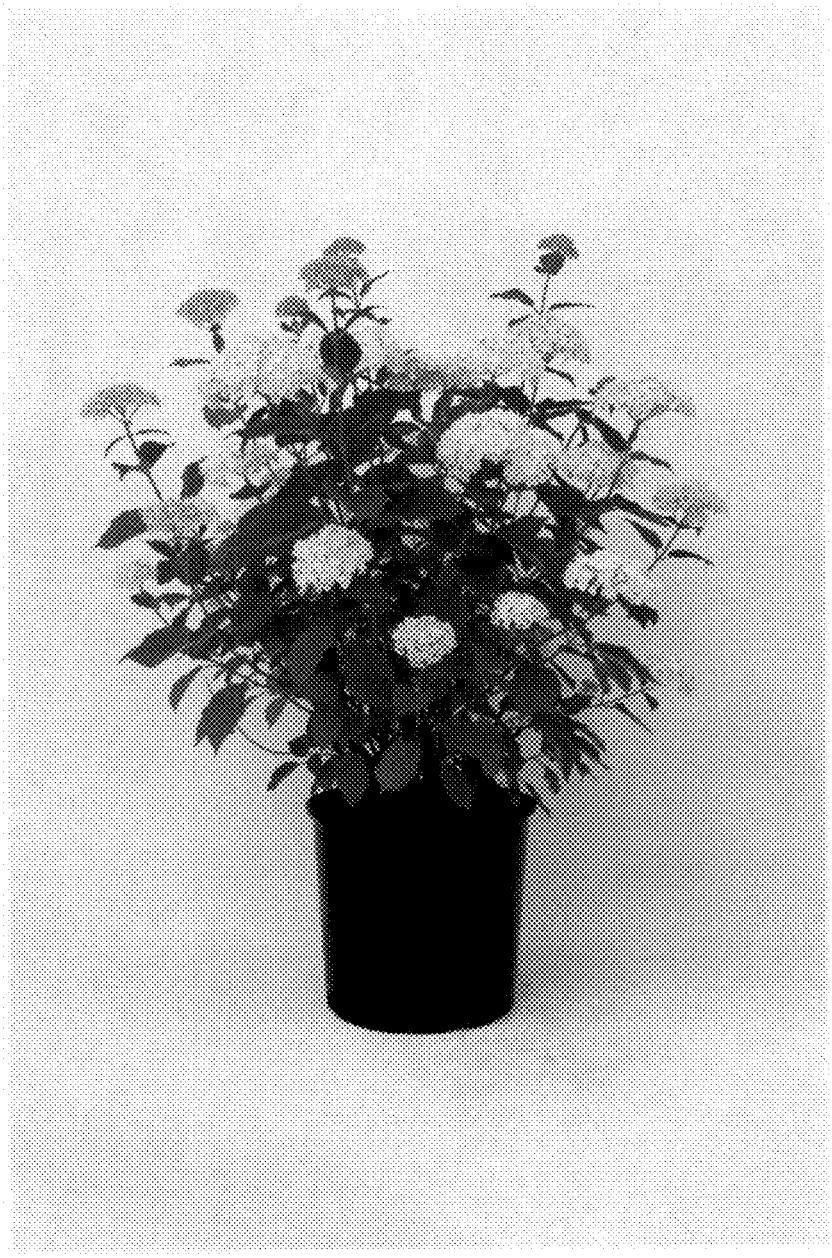

Latin name of genus and species of plant claimed: *Hydrangea arborescens.*

Variety denomination: 'Age3213ens'.

STATEMENT REGARDING PRIOR DISCLOSURES BY THE INVENTOR

The first offer for sale of the new variety was July 2024, in the United States of America, at the New Varieties Showcase at the Cultivate Trade Show in Columbus, Ohio, followed by the publication of the 2025 Star Roses and Plants Woody Ornamentals & Edibles Catalog released Oct. 7, 2024. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new cultivar originated in Cochranville, Pennsylvania in summer of 2015 in a controlled breeding program. The breeding program's objective was developing *Hydrangea* cultivars that improve growth habits and flower color. The new cultivar is the result of open pollination. The female parent (i.e., the seed parent) of the new cultivar is an unnamed seedling that is the product of the cross of *Hydrangea arborescens* 'NCHA2' (U.S. Plant Pat. No. 28,316) and *Hydrangea arborescens* 'Abetwo' (U.S. Plant Pat. No. 20,571). The male parent (i.e., the pollen parent) is unknown.

The parentage of the new variety can be summarized as follows:

('NCHA2' x 'Abetwo') x unknown

The new cultivar was discovered and selected as a single flowering plant within the progeny of the above stated open pollination. The final selection of the new variety was made in June 2020 in Cochranville, Pennsylvania.

The new variety has been found to undergo asexual propagation in Cochranville, Pennsylvania by terminal stem cuttings. Asexual propagation by terminal stem cuttings in Cochranville, Pennsylvania has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of *Hydrangea* plant of the present invention possesses the following combination of characteristics:

(a) forms bright white colored mophead-type flowers,
(b) provides green foliage, and
(c) displays a compact growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, plants of the new cultivar differ from the female parent variety (i.e., product of 'NCHA2' x 'Abetwo') in that the new cultivar has stronger stems preventing flopping, whereas the female parent variety does flop.

Moreover, the new variety can be readily distinguished from other similar non-parental varieties. Of the many commercially available *Hydrangea* cultivars, the most similar in comparison to the new cultivar is the 'Abetwo' variety. However, in comparison, plants of the new cultivar differ from plants of the 'Abetwo' variety at least because the new cultivar has sturdier stems with less flopping than the stems of the 'Abetwo' variety, and plants of the new cultivar have a more compact and tighter growth habit than plants of the 'Abetwo' variety.

BRIEF DESCRIPTION OF THE PHOTOGRAPHS

The accompanying photographs show, as nearly true as it is reasonably possible to make the same in color illustrations of this type, typical flower and foliage characteristics of a plant of the new cultivar. Colors in the photographs differ slightly from the color values cited in the detailed description, which accurately describes the colors of the 'Age3213ens' variety. The plant of the new cultivar was approximately two years old and was photographed in August 2023, while growing in a three-gallon container in Cochranville, Pennsylvania, U.S.A.

FIG. 1—illustrates a side view of the overall growth and flowering habit.

Figure 2:
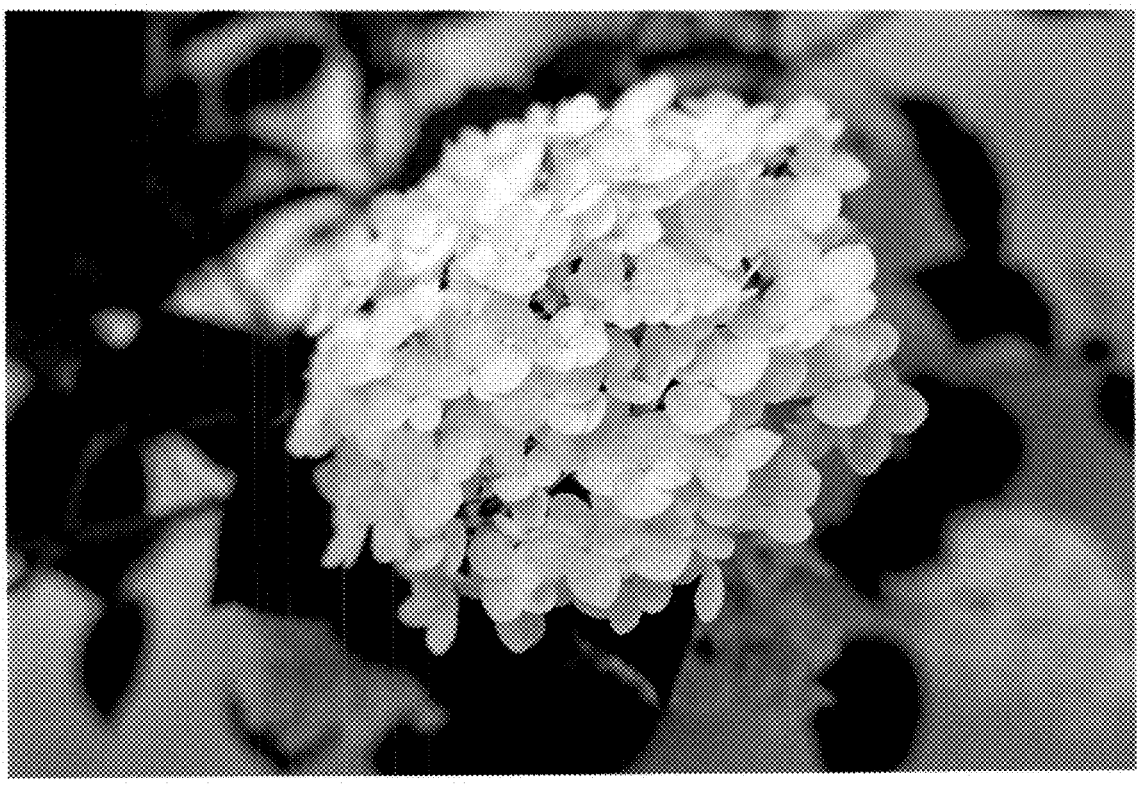

FIG. 2—illustrates a closeup view of the inflorescence.

DETAILED BOTANICAL DESCRIPTION

The chart used in the identification of the colors is that of The Royal Horticultural Society (The R.H.S. Colour Chart, 2015 edition), London, England, except where general color terms of ordinary significance are used. The terminology which precedes reference to the chart has been added to indicate the corresponding color in more common terms and The R.H.S. Colour Chart designation used herein represents the closest color observed on the majority of the specified botanical feature. The color values were determined in June 2024, under natural light conditions in Cochranville, Pennsylvania. The description is based on the observation of plants produced from cuttings from stock plants and grown in three-gallon containers for approximately two years in an outdoor nursery in Cochranville, Pennsylvania. Measurements and numerical values represent averages of typical plants.

Botanical classification: *Hydrangea arborescens* cultivar 'Age3213ens'.

Propagation:

*Type cutting*.—Terminal stem cuttings.

*Time to initiate roots during the summer*.—Approximately 14 days.

*Time to initiate roots during the winter*.—Approximately 21 days.

*Root description*.—White, fine, fibrous.

*Rooting habit*.—Moderate branching and density.

Plant description:

*Commercial crop time*.—Approximately 24 months from a rooted cutting to finish in a 3-gallon pot.

*Growth habit and general appearance*.—Deciduous shrub and upright growth habit.

*Hardiness*.—USDA Zones 3-8.

*Size*.—Height from soil level to top of plant plane: approximately 55.0 cm on average. width: approximately 60.0 cm on average.

*Branching habit*.—Freely branching. Pinching enhances branching. quantity of lateral branches per plant: approximately

*Branches*.—Shape: rounded. — strength: very strong. — length to base of inflorescence: approximately 40.0 cm on average. — diameter: approximately 5.0 mm on average. — length of central internode: approximately 9.0 cm on average. — texture of young stem: sparsely pubescent. — texture of mature stem: woody. — color of young stem: Yellow-Green Group 144C. — color of mature stem: Grey-Brown Group 199C. — quantity of lenticels per internode: approximately 14 on average. — size of stem's lenticel: typically 0.5 mm to 1.0 mm in diameter. — shape of stem's lenticel: round to elliptic. — color of stem's lenticel: Grey-Brown Group 199D. — mature surface texture of exfoliating bark: papyraceous. — color of exfoliated bark: Brown Group 200C.

Foliage:

*General description*.—Quantity of leaves per lateral branch: approximately 10 on average. — fragrance: none detected. — form: simple. — arrangement: opposite.

*Leaves*.—Aspect: flat. — shape: elliptic. — margin: serrated. — apex: acuminate. — base: rounded. — venation pattern: pinnate. — length of mature leaf: approximately 11.0 cm on average. — width of mature leaf: approximately 7.0 cm on average. — texture of upper surface: coriaceous, sparsely pubescent. — texture of lower surface: coriaceous, sparsely pubescent. — color of upper surface of young foliage: Green Group 137C with venation of Green Group 139C. — color of lower surface of young foliage: Yellow-Green Group 148B with venation of Yellow-Green Group 148D. — color of upper surface of mature foliage: Green Group 139A with venation of Green Group 138B. — color of lower surface of mature foliage: Greyed-Green Group 191A with venation of Yellow-Green Group 148D. — color of upper surface in the fall: Green Group 139A. — color of lower surface in the fall: Yellow-Green Group 147C. — dormant terminal leaf bud size: approximately 1.1 cm in length and approximately 4.0 mm in width. — dormant terminal leaf bud color. Greyed-Orange Group 166A.

*Petiole*.—Length: approximately 3.0 cm on average. — diameter: approximately 2.0 mm on average. — texture of upper and lower surfaces: sparsely pubescent. — color: Yellow-Green Group N148A.

Flowering description:

*Flower type and habit*.—Single fertile and sterile flowers arranged on large terminal panicles.

*Fragrance*.—None detected.

*Natural flowering season*.—Seasonal, continuously flowering from summer through fall in Cochranville, Pennsylvania.

*Lastingness of individual inflorescence on the plant.*—Approximately 6-8 weeks.

Inflorescence:

*General description.*—Height: approximately 7.0 cm on average. — width: approximately 14.0 cm on average. — shape: terminal mop-head. — quantity per plant: one per lateral or sublateral stem. — aspect: face upward. — quantity of fertile florets per inflorescence: approximately 300 on average. — quantity of sterile florets per inflorescence: approximately 300 on average.

*Peduncle.*—Strength: strong. — shape: rounded. — length: approximately 2.5 cm on average. — diameter: approximately 1.4 mm on average. — texture: moderately pubescent. — color: Yellow-Green Group 146D.

Floret description:

*General description.*—Type single, sterile and fertile flowers.

*Fertile flowers.*—Flower diameter: approximately 2.0 mm on average. — flower depth (height): approximately 2.0 mm on average. — flower bud length, just before opening: approximately 2.2 mm on average. — flower bud diameter, just before opening: approximately 2.0 mm on average. — flower bud shape, just before opening: orbicular. — flower bud color, just before opening: White Group 155C. — petal arrangement: rotate. — petal length: approximately 0.8 mm on average. — petal width: approximately 0.5 mm on average. — petal shape: obovate. — petal apex: obtuse. — petal base: truncate. — petal margin: entire. — petal texture of upper and lower surfaces: glabrous. — petal color: when first open, upper and lower surfaces: White Group 155C. when fully opened, upper and lower surfaces: Yellow-White Group 158D. — pedicel aspect: erect. — pedicel strength: strong. — pedicel length: approximately 1.0 mm on average. — pedicel diameter: typically less than 0.4 mm. — pedicel texture: glabrous. — pedicel color: White Group 155B.

*Sterile flowers.*—Flower diameter: approximately 1.0 cm on average. — flower depth (height): approximately 4.0 mm on average. — flower bud length, just before opening: approximately 2.2 mm on average. — flower bud diameter, just before opening: approximately 2.0 mm on average. — flower bud shape, just before opening: Orbicular. — flower bud color, just before opening: Yellow-Green Group 145B. — sepals: quantity per flower. typically 3 to 4. attitude: open and flat. intensity of overlapping sepals: zero to minimal. length: approximately 8.0 mm on average. width: approximately 8.0 mm on average. shape: broadly obovate. apex: broadly rounded. base: cuneate. margin: entire. texture, upper surface: glabrous. texture, lower surface: glabrous. color: when first open, upper and lower surfaces: White Group 155C. color: when fully opened, upper and lower surfaces: White Group NN155A. color: when fading or aging, upper and lower surfaces: White Group 155B. — pedicel: aspect: erect. strength: strong. length: approximately 1.0 cm on average. diameter: approximately 0.8 mm on average. texture: sparsely pubescent. color: White Group 155C.

*Reproductive organs, fertile flowers.*—Stamens: quantity per fertile flower: approximately 6 on average. filament quantity per fertile flower: approximately 10 on average. filament color: White Group 155C. anther shape: round. anther length: approximately 1.2 mm on average. anther color: White Group 155A. pollen amount: sparse. pollen color: Yellow-White Group 158B. pistil quantity per fertile flower: one. pistil length: approximately 1.0 mm on average. stigma shape: oval. stigma color: White Group 155A. style length: typically less than 0.5 mm. style color: White Group 155A. ovary color: White Group 155A.

Development:

*Seed and fruit production.*—Neither seed nor fruit production has been observed.

*Disease and pest resistance.*—Resistance to pathogens and pests common to *Hydrangea* has not been observed.

The new 'Age3213ens' cultivar has not been observed under all possible environmental conditions to date. Accordingly, it is possible that the phenotype may vary somewhat with variations in the environment, such as temperature, light intensity, and day length, without, however, any variance in genotype.

I claim:

1. A new and distinct variety of *Hydrangea* plant named 'Age3213ens' characterized by the following combination of characteristics:

(a) forms bright white colored mophead-type flowers, (b) provides green foliage, and (c) displays a compact growth habit;

substantially as herein shown and described.

* * * * *